(12) United States Patent
Heinecke

(10) Patent No.: US 7,442,849 B2
(45) Date of Patent: Oct. 28, 2008

(54) THIN FILM DELIVERY SYSTEM AND METHOD OF MANUFACTURE

(75) Inventor: Steven B. Heinecke, New Richmond, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 447 days.

(21) Appl. No.: 11/323,679

(22) Filed: Dec. 30, 2005

(65) Prior Publication Data

US 2007/0156075 A1 Jul. 5, 2007

(51) Int. Cl.
*A61F 13/00* (2006.01)
(52) U.S. Cl. .............................. 602/58; 602/41; 602/42; 602/52; 602/54
(58) Field of Classification Search ......... 604/304–308; 602/41–59; 128/888, 889; D24/189
See application file for complete search history.

(56) References Cited

U.S. PATENT DOCUMENTS

| | | | | |
|---|---|---|---|---|
| 2,532,011 A | 11/1950 | Dahlquist et al. | ......... | 154/53.5 |
| RE24,906 E | 12/1960 | Ulrich | ......... | 206/59 |
| 3,389,827 A | 6/1968 | Abere et al. | ......... | 220/53 |
| 3,645,835 A | 2/1972 | Hodgson | ......... | 161/146 |
| 4,112,213 A | 9/1978 | Waldman | ......... | 526/279 |
| 4,310,509 A | 1/1982 | Berglund et al. | ......... | 424/28 |
| 4,323,557 A | 4/1982 | Rosso et al. | ......... | 424/28 |
| 4,472,480 A | 9/1984 | Olson | ......... | 428/332 |
| 4,485,809 A | 12/1984 | Dellas | ......... | 128/156 |
| 4,513,739 A | 4/1985 | Johns | ......... | 128/156 |
| 4,595,001 A | 6/1986 | Potter et al. | ......... | 128/156 |
| 4,600,001 A | 7/1986 | Gilman | ......... | 128/156 |
| 4,737,410 A | 4/1988 | Kantner | ......... | 428/343 |
| 4,781,293 A | 11/1988 | Johns | ......... | 206/441 |
| 4,917,928 A | 4/1990 | Heinecke | ......... | 428/41 |
| 5,018,516 A * | 5/1991 | Gilman | ......... | 602/52 |
| 5,088,483 A | 2/1992 | Heinecke | ......... | 602/46 |
| 5,160,315 A | 11/1992 | Heinecke et al. | ......... | 602/57 |
| 5,266,371 A * | 11/1993 | Sugii et al. | ......... | 428/41.5 |
| 5,336,162 A * | 8/1994 | Ota et al. | ......... | 602/41 |
| 6,278,036 B1 | 8/2001 | Anhauser et al. | ......... | 602/41 |
| 6,362,388 B1 * | 3/2002 | Lucas | ......... | 602/57 |
| 6,685,682 B1 | 2/2004 | Heinecke et al. | ......... | 604/307 |
| 6,838,589 B2 * | 1/2005 | Liedtke et al. | ......... | 602/58 |
| 2002/0064619 A1 * | 5/2002 | Schroeder | ......... | 428/40.1 |
| 2002/0115954 A1 * | 8/2002 | Worthley | ......... | 602/57 |

FOREIGN PATENT DOCUMENTS

EP 0 051 935 B1 11/1986
WO WO 2006/092248 9/2006

OTHER PUBLICATIONS

Chapter 18; Handbook of Pressure Sensitive Adhesive Technology; Van Nostrand-Reinhold, 1982; pp. 384-403.
Boscheinen-Morrin et al.; Opsite Flexifix: An effective adjunct in the management of pain and hypersensitivity in the hand; Australian Occupational Therapy Journal (2001); 48, 170-175 (XP-002479765).
Opsite *Flexifix* Transparent Film Roll; Smith & Nephew product information; retrieved from internet (XP-002479766).

* cited by examiner

*Primary Examiner*—Kim M Lewis
(74) *Attorney, Agent, or Firm*—Nancy M. Lambert

(57) ABSTRACT

A carrier delivered dressing is disclosed which has a conformable backing with a pressure sensitive adhesive coated on a bottom face and removable carrier attached to the top face of the backing. A bond block material is positioned between the backing and the carrier. A cut line traverses both the carrier and the bond block material to form a tab.

31 Claims, 3 Drawing Sheets

THIN FILM DELIVERY SYSTEM AND METHOD OF MANUFACTURE

BACKGROUND OF THE INVENTION

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), and OP-SITE™ (T. J. Smith & Nephew, Hull, England).

The polymeric films used in those dressings and drapes, referred to as dressings below, are conformable, i.e., the films are extremely thin, flexible and supple. They are typically supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem such as those disclosed in U.S. Pat. No. 4,485,809; U.S. Pat. No. 4,600,001; and EPO Publication No. 0 051 935.

Carrier-type delivery systems such as those described in U.S. Pat. No. 6,685,682 offer an alternative delivery system for use with conformable thin films. The use of a removable carrier, which does not require tearing of the film after it has been placed on the patient, avoids the problems described above. The carrier also aids in accurate placement of the dressing on a patient.

OPSITE FLEXIFIX is a composite dressing provided in roll good form with a clear carrier and linear cut separation line along its length. To remove the carrier, the composite dressing must be stretched to reveal and allow the user to grasp the center portion of the carrier.

Therefore, additional carrier systems that provides ease-of-use and facilitate removal of the carrier during application of the dressing are still needed.

SUMMARY OF THE INVENTION

The present invention relates to pressure sensitive adhesive composite dressings comprising thin film backings coated on one side with a pressure sensitive adhesive, that are delivered by a removable carrier. The present invention also relates to methods of manufacturing such pressure sensitive adhesive composite dressings.

In one embodiment, an adhesive composite dressing is provided, comprising (a) a conformable backing having top and bottom faces; (b) a pressure sensitive adhesive coated on at least a portion of the bottom face of the backing; (c) a liner releasably adhered to the pressure sensitive adhesive opposite the backing; (d) a carrier releasably attached to at least a portion of the top face of the backing; (e) a bond block material positioned between the carrier and the top face of the backing; and (f) a cut line proximate the center of the article that traverses the length or width of the carrier; wherein the bond block material prevents bonding of the carrier to the backing to create a bond-free area adjacent to at least one side of the cut line.

In another embodiment, an adhesive medical article is provided, comprising a liner; a transparent film coated on a portion of at least surface with a pressure sensitive adhesive; a carrier; a bond block material positioned between the carrier and the top face of the backing; a cut line proximate the center of the article that traverses the length or width of the carrier; wherein the material prevents bonding of the carrier to the backing to create a bond-free area adjacent to at least one side of the cut line.

In another embodiment, an adhesive roll good is provided, comprising a liner; a transparent film coated on a portion of at least surface with a pressure sensitive adhesive; a carrier; a bond block material positioned between the carrier and the top face of the backing; a cut line proximate the center of the article that traverses the length or width of the carrier; wherein the material prevents bonding of the carrier to the backing to create a bond-free area adjacent to at least one side of the cut line.

A method of manufacturing an adhesive composite dressing is also provided, comprising (a) providing a conformable backing having top and bottom faces, a pressure sensitive adhesive on at least a portion of the bottom face of the backing and a liner on the pressure sensitive adhesive; (b) positioning a bond block material between the top face of the conformable backing and a carrier; (c) non-permanently heat sealing the carrier to the top face of the backing, the bond between the carrier and top face of the backing being greater than the bond between the liner and the pressure sensitive adhesive; and (d) die cutting a cut line through the carrier such that the bond block material positioned between the carrier and the top face of the backing is adjacent at least one side of the cut line; wherein the bond block material prevents bonding of the carrier to the backing to create bond-free area adjacent to at least one side of the cut line.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

BRIEF DESCRIPTION OF THE DRAWINGS

The invention may be further illustrated by reference to the accompanying drawings wherein.

DETAILED DESCRIPTION OF EMBODIMENTS OF THE INVENTION

The adhesive composite and methods of manufacturing the same of the present invention provide a carrier delivered dressing having a conformable backing with a pressure sensitive adhesive coated on a bottom face and an optional low adhesion coating on a top face, and which is supported by a removable carrier attached to the top face of the backing.

When applied, the release liner is first removed from the adhesive coated surface, the film and carrier are then placed on a patient and the carrier is then removed from the film, which is left on the skin.

In particular, the present invention provides an adhesive composite dressing comprising: (a) a conformable backing having top and bottom faces; (b) a pressure sensitive adhesive coated on at least a portion of the bottom face of the backing; (c) a liner releasably adhered to the pressure sensitive adhesive opposite the backing; (d) a carrier releasably attached to at least a portion of the top face of the backing, the carrier including a cut line proximate the center of the article that traverses the length or width of the carrier; and (e) a bond block material positioned between the carrier and the top face of the backing adjacent at least one side of the cut line wherein the material prevents bonding of the carrier to the backing to create bond-free area adjacent to at least one side of the cut line. The composite dressing may also include an optional low adhesion coating on the top face of the backing, in between the carrier and the top face of the backing.

The present invention also provides a method of manufacturing an adhesive composite dressing comprising the steps of: (a) providing a conformable backing having top and bottom faces, a pressure sensitive adhesive on at least a portion of the bottom face of the backing and a liner on the pressure sensitive adhesive; (b) positioning a material between the top face of the conformable backing and a carrier; (c) non-permanently heat sealing the carrier to the top face of the backing, the bond between the carrier and top face of the backing being greater than the bond between the liner and the pressure sensitive adhesive; (d) providing a cut line through the carrier such that the material positioned between the carrier and the top face of the backing is adjacent at least one side of the cut line; wherein the material prevents bonding of the carrier to the backing to create bond-free area adjacent to at least one side of the cut line.

Figure 1A:
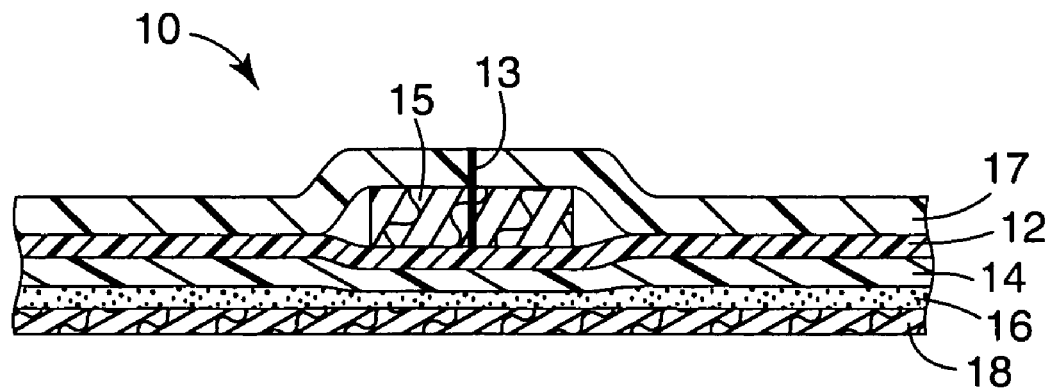
FIG. 1A is a cross-sectional side view of an illustrative embodiment of a dressing according to the present invention.
Figure 1B:
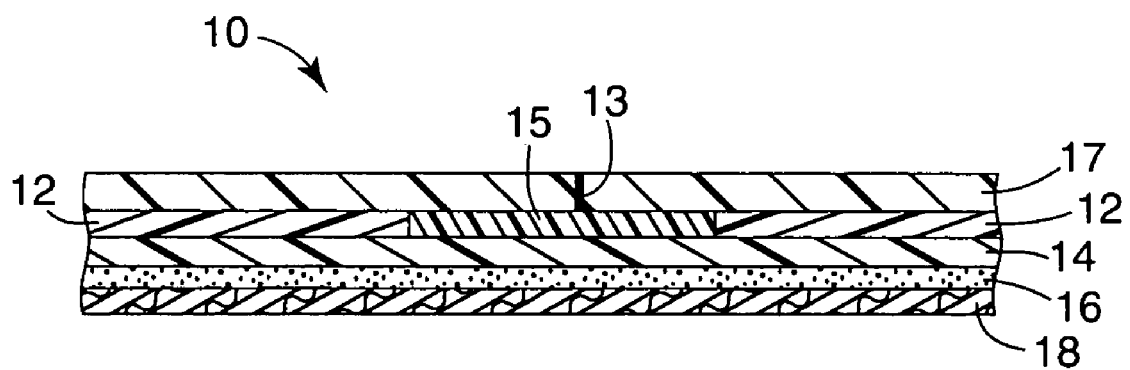
FIG. 1B is a cross-sectional side view of an illustrative embodiment of a dressing according to the present invention.
Figure 2:
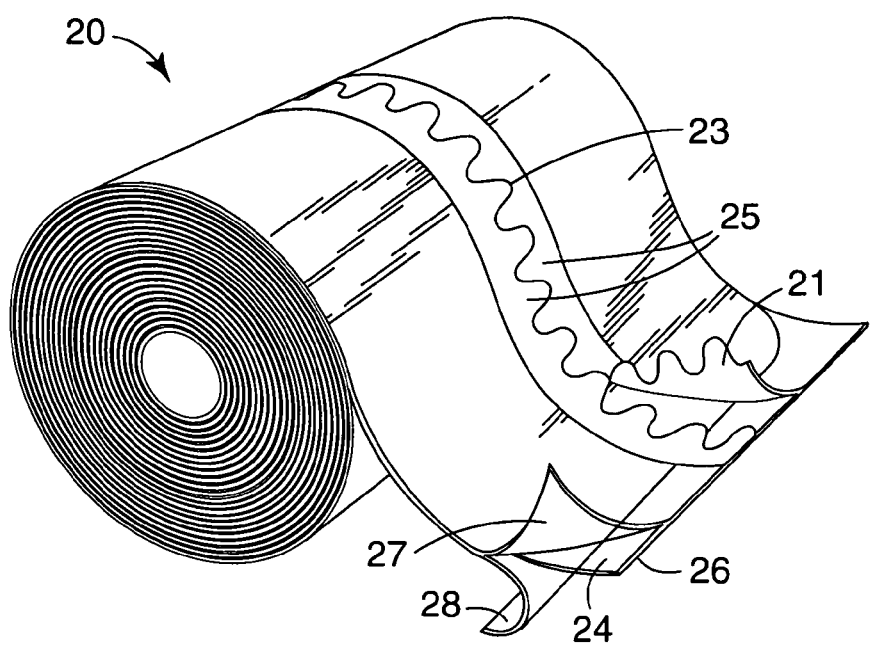
FIG. 2 is a perspective view of an illustrative embodiment of a dressing in roll good form according to the present invention.

FIGS. 1-3 depict preferred embodiments of dressings manufactured according to the present invention. The adhesive composite configuration of the present invention is useful in connection with any conformable backing having a pressure-sensitive adhesive coating on it. Representative backings include nonwoven fibrous webs, woven fibrous webs, knits, films and other familiar backing materials. The preferred backing materials are translucent or transparent polymeric films.

The invention is particularly useful in the field of pressure sensitive adhesive composites having high moisture vapor permeable film backings. Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backing is preferably conformable to anatomical surfaces. As such, when the backing is applied to an anatomical surface, it conforms to the surface even when the surface is moved. The preferred backing is also conformable to animal anatomical joints. When the joint is flexed and then returned to its unflexed position, the backing stretches to accommodate the flexion of the joint, but is resilient enough to continue to conform to the joint when the joint is returned to its unflexed condition.

A description of this characteristic of backings preferred for use with the present invention can be found in issued U.S. Pat. Nos. 5,088,483 and 5,160,315, the disclosures of which are hereby incorporated by reference. As discussed, particularly preferred backings are elastomeric polyurethane, polyester, or polyether block amide films. These films combine the desirable properties of resiliency, high moisture vapor permeability, and transparency found in preferred backings.

The preferred pressure sensitive adhesives which can be used in the adhesive composites of the present invention are the adhesives which are typically applied to the skin such as the acrylate copolymers described in U.S. Pat. No. RE 24,906, the disclosure of which is hereby incorporated by reference, particularly a 96:4 iso-octyl acrylate:acrylamide copolymer. Also preferred is an 70:15:15 isooctyl acrylate:ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827; 4,112,213; 4,310,509; and 4,323,557; the disclosures of which are hereby incorporated by reference. Inclusion of medicaments or antimicrobial agents in the adhesive is also contemplated, as described in U.S. Pat. Nos. 4,310,509 and 4,323,557 both of which are hereby incorporated by reference.

The preferred pressure sensitive adhesives described above preferably transmit moisture vapor at a rate greater to or equal to that of human skin. While such a characteristic can be achieved through the selection of an appropriate adhesive, it is also contemplated in the present invention that other methods of achieving a high relative rate of moisture vapor transmission may be used, such as pattern coating the adhesive on the backing, as described in U.S. Pat. No. 4,595,001, which is hereby incorporated by reference.

Liners which are suitable for use in the adhesive composites of the present invention can be made of supercalendered kraft paper, glassine paper, polyethylene, polypropylene, polyester or composites of any of these materials. The liners are preferably coated with release agents such as fluorochemicals or silicones. For example, U.S. Pat. No. 4,472,480, the disclosure of which is hereby incorporated by reference, describes low surface energy perfluorochemical liners. The preferred liners are papers, polyolefin films, polyethylene coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Florchheim, (Florchheim, Germany). The most preferred liner is silicone coated (1630) low density polyethylene available from Huhtamaki.

Other combinations of adhesives and liners are contemplated for use with embodiments according to the present invention. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

In the preferred embodiments according to the present invention, the choice of adhesives is limited to those that are safe to use on human skin, and preferably to those that are of the class known as "hypoallergenic". The preferred acrylate copolymers are adhesives of this class. Liners are available from a variety of manufacturers in a wide variety of proprietary formulations. Those skilled in the art will normally test those liners in simulated use conditions against an adhesive of choice to arrive at a product with the desired release characteristics.

The carrier material used to supply the carriers for dressings manufactured according to the present invention is preferably more rigid than the backing to prevent the backing from wrinkling during application. The carrier material can also be heat-sealable to the backing, with or without the low adhesion coating described below, for the purpose of manufacturing the preferred dressings. In general, the preferred carrier materials can include, but are not limited to, ethylene vinyl acetate copolymer or ethylene acrylic acid coated papers and polyester films. Preferably the carrier material is transparent to visualize the site during application. The most preferred carrier is EVA coated polyester available under the tradename SCOTCHPAK from 3M Company (St. Paul, Minn.).

The adhesive composites of the present invention also include a bond block material positioned between the top face of the backing and the carrier. The bond block material for dressings manufactured according to the present invention is preferably more rigid than the carrier to prevent the backing from wrinkling during application. The bond block material selected must prevent bonding between the carrier and of the top face of the backing, with or without the low adhesion coating described below, for the purpose of manufacturing the preferred dressings. In heat seal bond applications; the bond block material will not be heat-sealable at the heat temperatures used to manufacture the adhesive composite. In other words, the bond block material will have a melt temperature (Tg) that exceeds the temperature of the heat sealing process. In general, the preferred bond block materials can include, but are not limited to, plain bond papers, polyester films, fluoropolymer coatings, and silicone coatings. One example of a preferred bond block material is standard plain bond paper used in copying machines. The preferred paper stock is Omnibus 83260-D32, supercalendered kraft supplied by Glatfelter Paper, (Spring Grove, Pa.).

The adhesive composites of the present invention optionally also include a low adhesion coating on a top face of the backing, which is coated as a solution of polyvinyl N-octadecyl carbamate and a blend of silicone resins, as described in U.S. Pat. No. 6,685,682, which is incorporated by reference herein. When the carrier is heat seal-bonded to the backing, the preferred low adhesion coating is compatible with the heat seal bond between the carrier and the backing and also retains its low adhesion characteristics after heat sealing. While it is preferred that the top face of the adhesive composites of the present invention include a low adhesion coating, adhesive composites without such a coating with a carrier material attached thereto are also considered to be within the present invention.

The preferred low adhesion coating, polyvinyl N-octadecyl carbamate, is disclosed in detail in U.S. Pat. No. 2,532,011, the disclosure of which is hereby incorporated by reference for its teaching relating to the manufacture and coating of low adhesion coatings. It will also be understood that other coatings providing the low adhesion characteristics of the preferred coating could be substituted. The primary considerations in choosing any low adhesion coatings according to the present invention are their release characteristics and their compatibility with the attachment means between the carrier and the backing.

Illustrative Embodiments

Turning to FIGS. 1A and 1B, preferred embodiments of an adhesive composite dressing 10 comprise a backing 14 which is preferably conformable as described above; a pressure-sensitive adhesive 16 on a bottom face of the backing 14; a liner 18 attached to the exposed surface of pressure-sensitive adhesive 16; an optional low adhesion coating 12 on the top face of the backing; a carrier 17 attached to the top face of the backing 14; a cut line 13 traversing the carrier 17 and a bond block material 15 positioned between the carrier 17 and the top face of the backing 14 on both sides of a cut line 13.

In the preferred embodiment, the carrier 17 is attached to backing 14 with a heat seal bond. The heat seal bond between the carrier 17 and the backing 14 is stronger than the bond between the adhesive 16 and the liner 18. That difference ensures that the backing 14 remains attached to the carrier 17 when liner 18 is removed from the adhesive composite dressing 10. In other embodiments, the carrier can be adhesively attached to backing 14.

When used, a low adhesion coating 12 on the backing 14 also reduces dressing changes due to unwanted dressing removal when other tapes or devices are placed on the dressing 10 and removed. The low adhesion coating 12 also reduces the surface friction of the dressing 10 on linen or other fabrics, thereby offering additional protection against the accidental removal of dressings 10.

In FIG. 1A, the bond block material 15 is substantially more rigid than the carrier 17. The bond block material 15 is attached by a heat seal bond to the side of the carrier in contact with the top face of the backing 14. The bond block material can be attached to the carrier 17 by any suitable means, including but not limited to, adhesive attachment.

In an alternate embodiment shown in FIG. 1B, the bond block material 15 may be attached to the top face of the backing 14, for example, as a coating of material provided on the top face of the backing 14. In FIG. 1B, the bond block material 15 is coated on a portion of the top face of backing 14 in place of the low adhesion coating 12 provided on the remainder of the top face of backing 14. In other words, the low adhesion coating and the bond block material are strip coated to respective locations on the top face of the backing. Alternatively, the bond block material 15 can be coated on the low adhesion coating 12 that covers the entire top face of backing 14. In the embodiment shown in FIG. 1B, the cut 13 line can, but is not required to extend through the bond block material 15.

FIG. 2 shows a preferred embodiment of an adhesive composite dressing 10 of FIG. 1 in the form of a roll good 20 that comprises a backing 24 which is preferably conformable as described above; a pressure-sensitive adhesive 26 on a bottom face of the backing 24; a liner 28 attached to the exposed surface of pressure-sensitive adhesive 26; a carrier 27 attached to the top face of the backing 24; a cut line 23 traversing the length of the carrier 27 and a bond block material 25 positioned between a portion of the carrier 27 and the top face of the backing 24 on both sides of the cut line 23. The bond block material 25 is shown with a grid on its top surface which can be used to assist in measuring the length of dressing needed.

Carrier 27 and bond block material 25 include a nonlinear cut 23 that traverses the entire surface of the carrier 17 in at least one direction. The nonlinear cut 23 may be provided in the cross-web or down-web direction. In a preferred embodiment, the nonlinear cut 23 traverses the carrier 27 and bond block material 25 in the down-web direction.

The nonlinear cut 23 provides a tab 21 that creates a beginning point at which the carrier 27 may be easily lifted from backing 24 and peeled. Although cut 23 may also be a linear cut which is known in the art, the preferred embodiment includes a nonlinear cut. Nonlinear cuts form a more distinct tab 21 to facilitate removal of the carrier 27. Nonlinear cuts also provide more support for the backing 24 and carrier 27 because nonlinear cuts allow the carrier to partially fold at the cut line to raise the tab 21 from the top face of the backing 24 while at the same time preventing the backing 24 from adhering to itself during application. In a preferred embodiment, the nonlinear cut 23 is a sinusoidal cut as shown in FIG. 2. However, any nonlinear cut including a zig zag or nonsymmetrical nonlinear cut would also provide sufficient support to the carrier 27 and backing 24 when placing the dressing.

Liner 28 and carrier 27 both preferably include edges that extend beyond the perimeter of backing 24 as shown in FIG. 2 to provide a means of applying the backing/carrier/adhesive composite without contacting the adhesive 26. The edges allow the user to manipulate the adhesive composite dressing 10 (from roll good 20) during placement of the dressing 10 on a substrate.

Figure 3A:
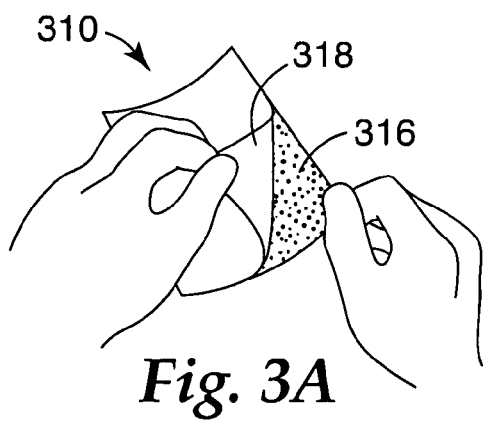
FIG. 3A is a perspective view of the dressing of FIG. 1 where the user is removing the liner.

Placing dressing 310 shown in FIG. 3A involves first removing the liner 318 from the adhesive composite dressing 310 leaving the carrier 317/backing 314/pressure sensitive adhesive 316 intact. By holding the dressing 310 at the adhesive-free edges, one may place the dressing 310 on a substrate by adhering the pressure sensitive adhesive 316/backing 314 composite to the area of a substrate. In a preferred embodiment, both the carrier 317 and the backing 314 are translucent or transparent, allowing the user to view the area on the substrate to which the dressing 310 will be attached.

Figure 3B:
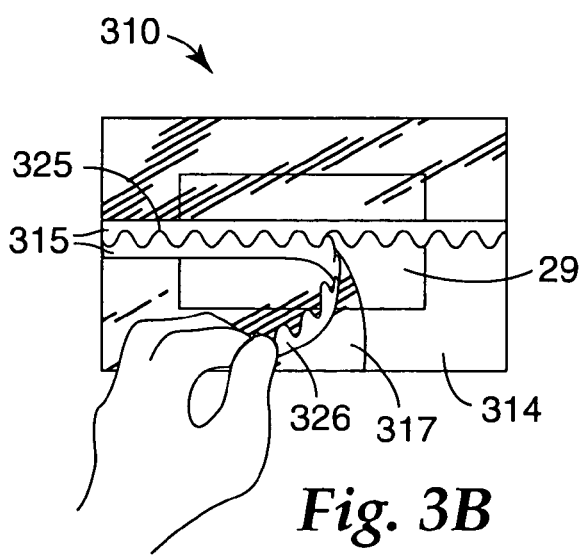
FIG. 3B of top plan view of the dressing of FIG. 1 where the user is removing the carrier.

As shown in FIG. 3B, the carrier portion of the carrier 317 is then removed once the dressing 310 is adhered to a surface by holding the tab 326 formed by bond block material 315 at nonlinear cut 325. Dressing 310 is shown with a substantially continuous nonlinear cut 325 through the bond block material 315 and carrier 317. Dressings may employ more than one nonlinear cut 325 to facilitate removal of the carrier 317 from the top of the backing 314. Dressings of the present invention may also include substantially discontinuous nonlinear cuts (not shown) so long as the bond block material 315 continues to form a tab on the carrier with the same functionality as described above.

FIG. 3B shows dressing 310 attached to a substrate including an absorbent pad 29 disposed below the center of the dressing 310. Absorbent pad 29 can be manufactured of a number of materials including, but not limited to, woven or nonwoven cotton or rayon. Absorbent pad 29 is useful for containing a number of substances, including antimicrobial agents, drugs for transdermal drug delivery, chemical indicators to monitor hormones or other substances in a patient, etc. Furthermore, although absorbent pad 29 is shown as centered on dressing 310, it can take any appropriate shape and/or can be located off-center on the dressing 310 as desired. Further, absorbent pad 29 is shown as part of the substrate located beneath the adhesive composite dressing 310, the absorbent 29 may be attached to adhesive composite dressing 310 on the bottom face of the backing 314 during manufacture.

In addition, it will also be appreciated that any of the dressings of the present invention may include additional tape strips or other structures useful for securing devices (e.g., tubes, catheters) to a patient, as described in U.S. Pat. No. 5,160,315, the disclosure of which is herein incorporated by reference.

Preferred Methods of Manufacture

In the preferred method, the carrier material and bond block material are die cut to form the nonlinear cut in the center of the carriers on the preferred dressings. In the preferred embodiments, the die cutting is accomplished using rotary die cutting equipment which is well known to those skilled in the art.

As stated above, it is desirable for the present invention that the bond between the carrier and the backing be more tenacious than the bond between the liner and the backing. Thus, the manufacturer must be able to exhibit control over the tenacity of the bonds. Heat sealing provides the manufacturer with increased control over the tenacity of the resulting bond as compared to extruding. Extruding involves spreading molten material over a substrate. To extrude, the material must obviously be heated to a temperature which causes the material to melt and become liquid. The manufacturer is therefore limited with regard to the minimum temperature which may be used to extrude a given material. Thus, a decreased temperature could not be used to limit the tenacity of an extruded bond. In contrast, heat sealing involves heating two materials and laminating the materials together. However, the materials do not need to be heated to a temperature which causes either of the materials to turn molten. The tenacity of a heat sealed bond is controlled by adjusting the temperature which the materials are heated and by adjusting the duration of the heating process. Since materials may be heat sealed, using greater temperature variability, heat sealing allows greater control over the tenacity of a bond as compared to extruding.

Additional control over the heat sealing process can be accomplished a number of ways. It can include cavities in the heated rolls used in heat sealing or other means, such as texturing the nip rolls which compress the adhesive composite web against the heated roll during processing. Those methods are described in greater detail below.

After the heat sealing step has been performed, the adhesive composite web is converted into finished product. In the preferred methods, the web now consists of the carrier material heat sealed to the backing, except in the location of the bond block material. The web further has an adhesive and liner on its opposing side. That web is preferably directed into a rotary die sheeting station that cuts the dressing with a nonlinear cut along the length of the web and then cuts the dressings out of the web and pulls the weed or waste material away for disposal. Preferably, the individual dressings are fed directly into a packaging station which packages the dressings for sterilization and delivery to customers.

Figure 4:
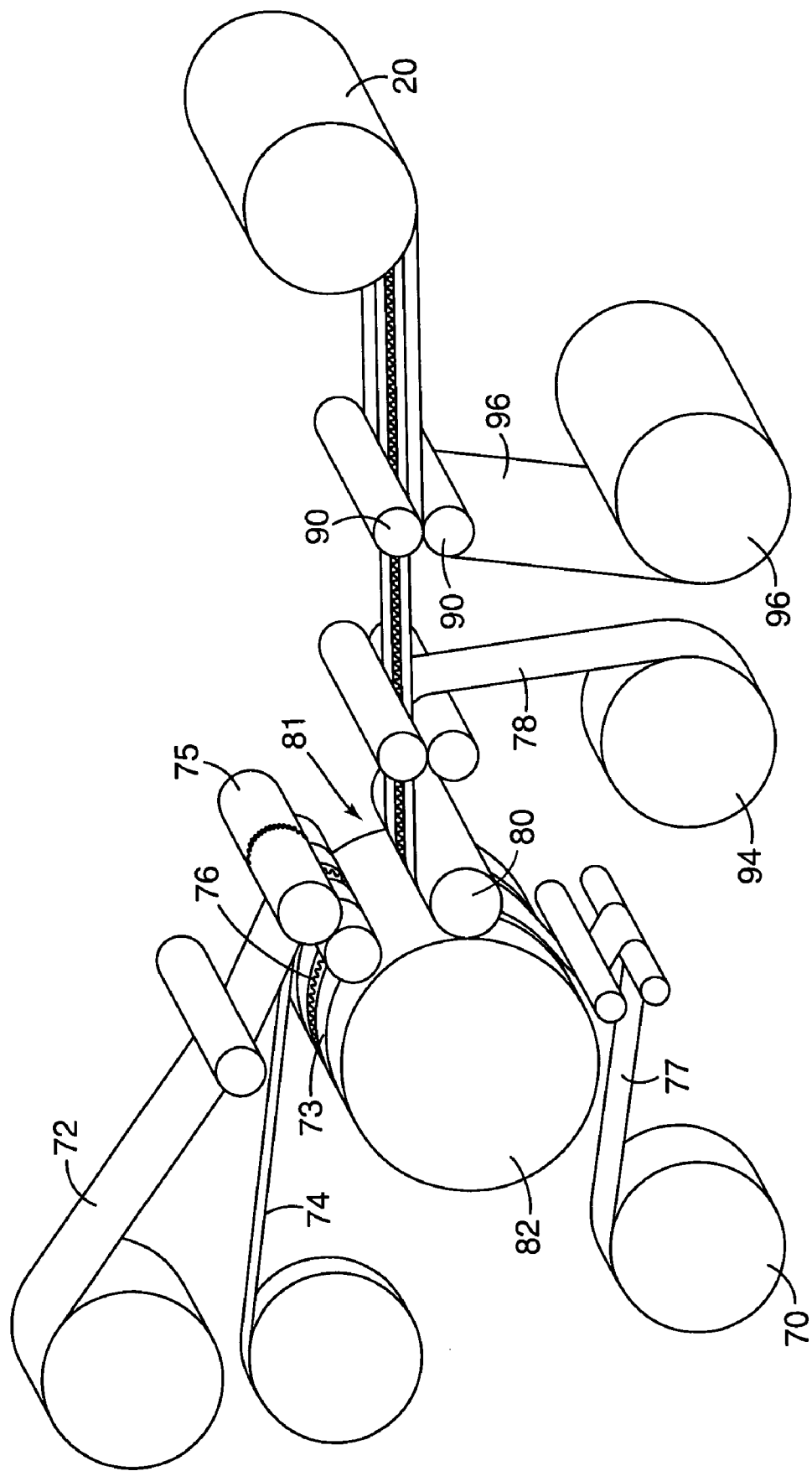
FIG. 4 is a schematic diagram in perspective of one preferred method of manufacturing dressings according to the present invention.

FIG. 4 depicts a schematic diagram of web fed rotary processing equipment for producing dressings according to the preferred methods of the present invention. The details of designing such equipment will be well known to those skilled in the art. Commercially available rotary web processing equipment including control depth die cut systems useful for practicing the method of the present invention can be obtained from, for example, the Mark Andy Company (St. Louis, Mo.) and Bernal Rotary Systems (Troy, Mich.).

In FIG. 4, roll 72 preferably comprises a heat sealable carrier material (also designated 72) as described above with the heat seal side 73 threaded as shown. The carrier material includes a bond block material 74 on the heat seal side threaded with the carrier material 72 as shown. Downstream, die cut roll 75 control depth die cuts the carrier material 72 and the bond block material 74 to form a substantially continuous nonlinear cut 76 in the web. The carrier material 72/bond block material 74 is then wrapped around a heated roll 82 as shown.

The second input roll 70 comprises the low adhesion coating/backing/backing (pressure sensitive) adhesive/liner composite (also 70) according to the present invention. The low adhesion coating/backing portion 77 is wound in and a waste liner 78 is wound out as shown from waste liner roll 94. The web from input roll 70 is threaded between the nip 81 formed between nip roll 80 and heated roll 82.

After removal of waste liner 78, product liner 96 from roll 96 is laminated to the adhesive composite 70 at the nip formed between the rolls 90. The finished product roll good 20 is released from the nip created by rolls 90.

In alternative embodiments of the web fed rotary process (not shown), the carrier material roll can be provided with its heat sealable side wound out. In addition, the control depth die cutting can be performed at the same station as the heat lamination. It should be understood by those skilled in the art that the schematic diagram contained in FIG. 4 represent one possible equipment configuration only and should not be construed as limiting the method of the present invention.

The following non-limiting examples will further illustrate the articles and methods of the present invention. All parts and percentages are expressed as parts by weight unless otherwise indicated.

EXAMPLE 1

Twenty-five grams per square meter of a pressure sensitive adhesive prepared in accordance with U.S. Pat. No. Re. 24,906, comprising a copolymer of 96% units of isooctyl acrylate and 4% units acrylamide was applied to a 60 pound bleached release liner, two side coated, silicone paper (2-60BKG 157/99AMM, Loparex, Willowbrook, Ill.) and the adhesive surface was laminated to 0.85 mil (22 micron) film of ESTANE 58309NAT022 polyurethane resin (Noveon, Cleveland, Ohio) to form the backing for the dressings. At that point, the backing/backing (pressure sensitive) adhesive/liner composite was completed.

The next step was to coat a low adhesion layer on the backing to provide the tape-over feature of the present invention. Using a Gravure station, a 6% solids solution (20 parts silicone and 80 parts polyvinyl N-octadecyl carbamate) was coated on the polyurethane (non-adhesive) side of the composite using a 120 line pyramid knurl and dried. The solution comprised:

1) a silicone resin blend of SS4300 at 95% units and SR-0545 at 5% units, both from General Electric (Waterford, N.Y.) provided in 90% toluene (by weight); and 2) a backsizing solution in accordance with U.S. Pat. No. 2,532,011, comprising polyvinyl N-octadecyl carbamate 5% solids in xylene-toluene (22%-78% by weight).

The low adhesion coating/backing/backing (pressure sensitive) adhesive/liner composite web was then slit to 10 cm to make the desired width of roll product.

A transparent carrier material, 12 cm wide (SCOTCHPAK ES470; 3M) and a (bond blocking material printed with a ruler) 160 mm wide paper (Omnibus 83260-D32, Glatfelter, Spring Grove Pa.) was centered and laminated to the PVA side of the carrier, and was then die cut through the carrier and tab, to form the nonlinear center (sinusoidal) cut delivery tab in the machine direction.

The PVA side of the carrier material was heat laminated to the backing at 80 degrees C. and 16 meters per minute (over the low adhesion coating) composite and paper tab. The coating liner was removed and replaced with a wider (12.7 cm) silicone liner (printed white polyethylene film, LDPE with 1730 silicone, Huhtamaki Florchhiem, Florchhiem, Germany) making rolls of 10 meters in length using rotary equipment with the configuration shown in FIG. 4. The station modified for heat sealing used a heated roll manufactured by Tokuden Ltd. (Kyoto, Japan).

The final product carrier and liner were cut wider than the backing and adhesive laminate to facilitate easy removal of the liner first without touching the adhesive surface.

In view of the foregoing description, it will be apparent that the methods and composite dressings of the invention are not limited to the specific details set forth herein for purposes of illustration, and that various other modifications are equivalent for the stated and illustrated functions without departing from the spirit of the invention and the scope thereof as defined in the appended claims.

What is claimed is:

1. An adhesive composite dressing comprising:
   (a) a conformable backing having top and bottom faces;
   (b) a pressure sensitive adhesive coated on at least a portion of the bottom face of the backing;
   (c) a liner releasably adhered to the pressure sensitive adhesive opposite the backing;
   (d) a carrier releasably attached to at least a portion of the top face of the backing;
   (e) a bond block material positioned between the carrier and the top face of the backing; and
   (f) a cut line proximate the center of the dressing that traverses the length or width of the carrier
   wherein the bond block material prevents bonding of the carrier to the backing to create a bond-free area adjacent to at least one side of the cut line.

2. The adhesive composite of claim 1 wherein the bond block material is more rigid than the carrier.

3. The adhesive composite of claim 1, wherein the carrier is attached by heat seal bond to the top face of the backing.

4. The adhesive composite of claim 1, wherein the bond block material is attached by heat seal bond to the carrier on the side of the carrier facing the film.

5. The adhesive composite of claim 1, wherein the cut line is substantially continuous.

6. The adhesive composite of claim 1, wherein the cut line is nonlinear.

7. The adhesive composite of claim 6, wherein the cut line is sinusoidal.

8. The adhesive composite of claim 1, wherein the bond block material is a coating on the top face of the backing.

9. The adhesive composite of claim 1, wherein the adhesive composite dressing further comprises a low adhesion coating on the top face of the backing.

10. The adhesive composite dressing of claim 9, wherein the low adhesion coating comprises a polyvinyl carbamate low adhesion coating.

11. The adhesive composite dressing of claim 1, wherein the backing is selected from the group consisting of polyurethane film, polyester film, polyether block amide film, and combinations thereof.

12. The adhesive composite dressing of claim 1, wherein the carrier is selected from the group consisting of polyester film, paper, and combinations thereof.

13. The adhesive composite dressing of claim 1, wherein the bond block material is paper.

14. The adhesive composite dressing of claim 1, wherein the backing and pressure sensitive adhesive transmit moisture vapor at a rate of at least 300 $g/m^2/24$ hrs/$37°$ C./100-10% RH.

15. An adhesive medical article, comprising
a liner;
a transparent film coated on at least a portion of the surface with a pressure sensitive adhesive;
a carrier;
a bond block material positioned between the carrier and the top face of the backing;
a cut line proximate the center of the article that traverses the length or width of the carrier; and
wherein the material prevents bonding of the carrier to the backing to create a bond-free area adjacent to at least one side of the cut line.

16. The adhesive medical article of claim 15, wherein the cut line is in the form of a serpentine.

17. The adhesive medical article of claim 15, wherein the bond block material has a grid printed on its surface.

18. An adhesive roll good, comprising
a liner;
a transparent film coated on a portion of at least surface with a pressure sensitive adhesive;
a carrier;
a bond block material positioned between the carrier and the top face of the backing;
a cut line proximate the center of the roll good that traverses the length or width of the carrier; and
wherein the material prevents bonding of the carrier to the backing to create a bond-free area adjacent to at least one side of the cut line.

19. A method of manufacturing an adhesive composite dressing comprising the steps of:
 (a) providing a conformable backing having top and bottom faces, a pressure sensitive adhesive on at least a portion of the bottom face of the backing and a liner on the pressure sensitive adhesive;
 (b) positioning a bond block material between the top face of the conformable backing and a carrier;
 (c) non-permanently heat sealing the carrier to the top face of the backing, the bond between the carrier and top face of the backing being greater than the bond between the liner and the pressure sensitive adhesive; and
 (d) die cutting a cut line through the carrier such that the bond block material positioned between the carrier and the top face of the backing is adjacent at least one side of the cut line;
 wherein the bond block material prevents bonding of the carrier to the backing to create bond-free area adjacent to at least one side of the cut line.

20. The adhesive composite of claim 19 wherein the bond block material is more rigid than the carrier.

21. The adhesive composite of claim 19, wherein the carrier is attached by heat seal bond to the top face of the backing.

22. The adhesive composite of claim 19, wherein the bond block material is attached by heat seal bond to the carrier on the side of the carrier facing the film.

23. The adhesive composite of claim 19, wherein the cut line is substantially continuous.

24. The adhesive composite of claim 19, wherein the cut line is nonlinear.

25. The adhesive composite of claim 24, wherein the cut line is sinusoidal.

26. The adhesive composite of claim 19, wherein the bond block material is a coating on the top face of the backing.

27. The adhesive composite of claim 19, wherein the adhesive composite dressing further comprises a low adhesion coating on the top face of the backing.

28. The adhesive composite dressing of claim 27, wherein the low adhesion coating comprises a polyvinyl carbamate low adhesion coating.

29. The adhesive composite dressing of claim 19, wherein the backing is selected from the group consisting of polyurethane film, polyester film, polyether block amide film, and combinations thereof.

30. The adhesive composite dressing of claim 19, wherein the carrier is selected from the group consisting of polyester film, paper, and combinations thereof.

31. The adhesive composite dressing of claim 19, wherein the bond block material is paper.

\* \* \* \* \*